Figure 1:
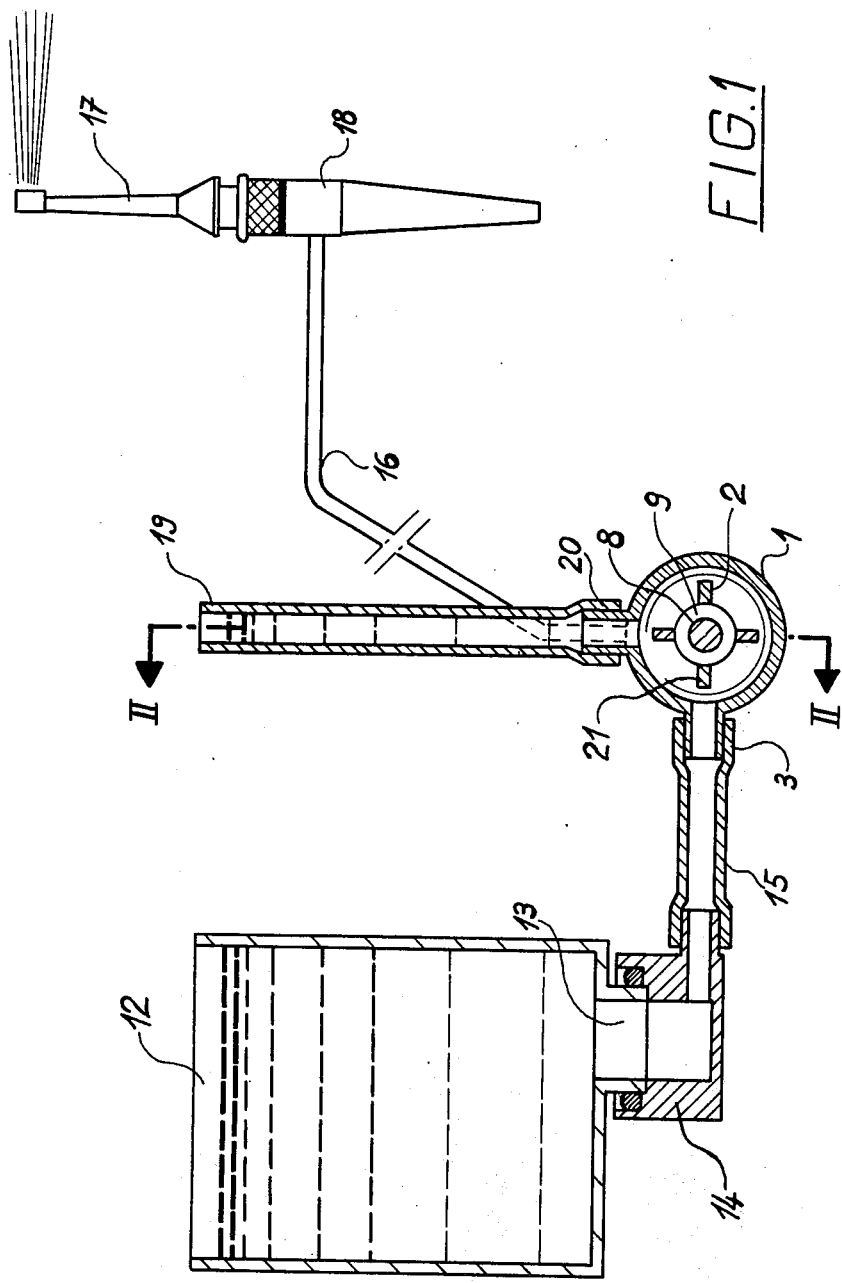

United States Patent [19]
Moret et al.

[11] 3,952,736
[45] Apr. 27, 1976

[54] HAND-OPERATED BODY CARE APPLIANCE

[75] Inventors: Michel Antoine Moret, Chene-Bourg, Gva; Pierre-Jean Jousson, Geneva; Jean-Pierre Musy, Puplinge, Gva, all of Switzerland

[73] Assignee: 4 P Limited, United Kingdom

[22] Filed: Dec. 19, 1974

[21] Appl. No.: 534,380

[30] Foreign Application Priority Data
Dec. 21, 1973 Switzerland.................... 17991/73
Dec. 21, 1973 Switzerland.................... 17992/73

[52] U.S. Cl. .............................................. 128/66
[51] Int. Cl.² ........................................ A61H 9/00
[58] Field of Search................ 128/62 A, 66, 230; 32/58

[56] References Cited
UNITED STATES PATENTS
| | | | |
|---|---|---|---|
| 3,393,673 | 7/1968 | Mattingly | 128/66 |
| 3,453,969 | 7/1969 | Mattingly | 128/66 X |
| 3,861,383 | 1/1975 | Kovach | 128/66 |

*Primary Examiner*—Lawrence W. Trapp
*Attorney, Agent, or Firm*—Robert E. Burns; Emmanuel J. Lobato; Bruce L. Adams

[57] ABSTRACT

A hand-operated appliance for body care by means of an intermittent liquid jet, in particular for massaging the gums and for cleaning the teeth, has a liquid pump which comprises a working chamber connected to an outlet fitted with a spray nozzle, a piston reciprocated therein by an electric motor, an inlet chamber connected to an inlet pipe fed from a liquid reservoir, and an inlet valve located in the connecting aperture between the inlet chamber and working chamber. The inlet valve is biased towards the open position by a spring the force of which is less than the pressure exerted during the working stroke of the piston and tending to close the valve. The liquid reservoir is connected by the inlet chamber of the pump to an ascending pipe acting as an air-vent pipe which is arranged vertically, is open at the top and is branched from the inlet chamber.

17 Claims, 4 Drawing Figures

HAND-OPERATED BODY CARE APPLIANCE

The invention relates to a hand-operated appliance for body care by means of an intermittent liquid jet, in particular for massaging the gums and cleaning the teeth, with a liquid pump which comprises a working chamber connected to an outlet pipe with a piston located therein and driven by a motor, an inlet chamber connected to an inlet pipe and an inlet valve located in the connecting aperture between the inlet and working chambers, with a liquid reservoir connected to the inlet pipe and a spray nozzle conneted to the outlet pipe.

In hand-operted appliances of this type, the problem exists of venting the hydraulic system, in particular the inlet chamber of the pump, before the appliance is set in operation, sufficiently so that after the connection of the full reservoir to the pump, the liquid fills the inside of the pump as completely as possible whilst rapidly expelling the air present in the pump. Only then is it ensured that after starting the pump and opening the stop valve generally provided on the spray nozzle, the supply of liquid begins immediately and at full volume. This venting problem causes difficulties in particular in those hand-operated appliances which, as is generally the case, have an inlet valve spring-loaded in the closing direction, i.e. which is closed in its inoperative position. If the hand-operated appliance is to be used after an interval, then generally it is substantially empty of liquid. If, for the purpose of starting the apparatus, the full liquid reservoir is connected to the pump, generally the water cannot flow into the inlet chamber of the pump, because the latter is largely filled with air and closed by the spring-loaded inlet valve. Thus, the air has virtually no possibility of escaping from the inlet chamber. Under these circumstances of completely unsatisfactory venting of the hydraulic system, when switching on the apparatus, an immediate supply of liquid by the pump at full volume is not guaranteed and after opening the stop valve, the user must generally wait impatiently for a prolonged period of time until the air present in the hydraulic system is expelled and the pump has filled with liquid. During this period, there is no supply of liquid or, however, there is only a weak irregular liquid jet.

Even if the pump has a pressure-regulating device, which, when it is not set to maximum pressure, frees a secondary pipe between the working chamber and inlet chamber of the pump to a greater or lesser extent, the possibility of rapid and reliable venting, in particular of the pump inlet chamber, after the connection of the full reservoir to the pump, depends on whether or not and how quickly air pockets may escape by way of the working chamber and outlet pipe, provided that the latter is not closed.

It is the object of the invention to solve this problem of venting in a hand-operated appliance of the afore-described type in the most simple manner.

For this prupose, the hand-operated appliance according to the invention is characterised in that the liquid reservoir is connected by way of the inlet chamber of the pump to an ascending pipe acting as an airvent pipe, which is arranged vertically, is open at the top and branches off from the inlet chamber.

Due to this very simple measure, the reservoir connected to the pump, the pump inlet chamber and the ascending pipe form a system of communicating pipes, which guarantees the complete filling of the inlet chamber, when the full reservoir is connected to the inlet pipe of the pump. The air may then escape completely from the inlet chamber through the ascending pipe, the liquid level in the ascending pipe assuming the same level as in the reservoir.

Advantageously, the inlet chamber is constructed, for example by the provision of suitable baffles, such that during filing of the inlet chamber, there is a good circulation around the inlet valve.

For reasons of space, the height of the ascending pipe may be less than that of the reservoir, a float provided with openings for the passage of air then being located in the ascending pipe, which float, in its raised position, i.e. when the ascending pipe is full, closes off the upper opening of the latter.

In hand-operated appliances, which are provided with a stop valve in the liquid outlet pipe or in the spray nozzle, for the purpose of opening or closing the pipe leading to the nozzle aperture and which for reasons of simplicity have no liquid return pipe leading to the liquid reservoir, by which the liquid cycle of the pump is short-circuited when the supply of liquid to the spray nozzle is interrupted, a further problem occurs: it must be ensured by appropriate means that at the time of switching on, the pump motor starts reliably under any circumstances, especially since the starting torque of a small motor in hand operated appliances of this type is less than the rated torque of the motor. However, if, on putting the hand-operated appliance in operation, the hydraulic system between the inlet valve, which in known hand-operated appliances is generally closed by a closing spring in the inoperative position and the likewise closed stop valve is completely filled with liquid, then in practice, the motor could not start up at the time of switching on if it were not ensured that the liquid expelled during the working stroke of the piston could escape somewhere. In order to solve this starting problem, it is known to mechanically interconnect the electric switch for the pump motor and the pressure-regulating device of the pump and to actuate them by means of a common control member such that when switching on the motor, the minimum pressure is necessarily set, before the pressure is subsequently increased if necessary by a further displacement of the control member. However, a connection of this type between the electric switch and the pressure-regulating device represents a relatively complicated mechanical arrangement which is prone to disturbances. Moreover, starting up of the pump is not guaranteed if, after prior use, the electrical plug is simply pulled out of the socket for the purpose of switching the apparatus off and is reinserted in the socket for once more setting the apparatus in operation, since in these cases, the pressure-regulating device is generally in any intermediate position, but not in the position corresponding to minimum pressure. The same is true in the case of a power failure.

In another known hand-operated apparatus without a liquid return pipe, the hydraulic system is provided with an additional spring-loaded auxiliary piston, which is able to give under the pressure of the liquid in the manner of a damper, when the liquid pump is switched on and the stop valve is closed. However, in this case, the dimensions of the spring acting on the auxiliary piston are very critical and furthermore, an auxiliary piston of this type increases the production costs of the hand-operated appliance.

In order to solve this starting-up problem in the most simple manner in a hand-operated appliance which has no liquid return pipe and is provided with a stop valve in the outlet pipe, in a preferred embodiment of the invention, the inlet valve is constructed and arranged such that it assumes its open position in the inoperative condition, when the pump is switched off. In this manner it is achieved that in the inoperative position of the appliance, the hydraulic system, in particular including the working chamber of the pump, is not closed, but is connected by way of the open inlet valve and the inlet chamber to the ascending pipe and the open liquid reservoir. Therefore, when switching on the pump, during the first part of the working stroke of the pump piston, liquid may escape from the working chamber through the inlet valve which is still open, which is only closed after a certain delay under the action of the liquid pressure. In this manner, there is no necessity for the motor to start up under load and the relatively low starting torque of the motor is quite sufficient for the latter to accelerate quickly to its operating speed. When the pump is completely filled with liquid, i.e. when it is operating at maximum pressure, as tests showed, the inlet valve then operates in a manner which is exactly as trouble-free as hitherto known inlet valves actuated by a closing spring; i.e. the inlet valve is opened during each suction stroke of the piston and closed during each working stroke.

The inlet valve is preferably subject to the action of a valve spring acting in the opening direction, which, when the apparatus is switched off, keeps the valve in its open position appropriately determined by a stop. The strength of this valve spring should be as low as possible, such that its compression during the closing movement of the valve under the action of the liquid pressure requires only the lowest possible force.

The arrangement may also be provided such that since there is no valve opening spring, in the normal operating position of the pump, the inlet valve is arranged vertically with the closure member pointing downwards, so that it normally assumes its open position under the action of gravity. In this case, the working chamber of the pump is arranged vertically below the inlet chamber.

A valve of this type which is open in its inoperative position has the further advantage that after connection of the full liquid reservoir, the liquid entering the pump may pass at least partly out of the inlet chamber through the open inlet valve into the working chamber, the inside of the inlet chamber being especially constructed such that there is a complete circulation around the inlet valve.

The ascending pipe has the further advantage that it represents a small reservoir located in the immediate vicinity of the inlet valve with only a slender and therefore low inertia head of liquid, which moves under the action of the piston virtually free from lag and therefore also accelerates and improves the supply of the pump during operation.

Figure 2:
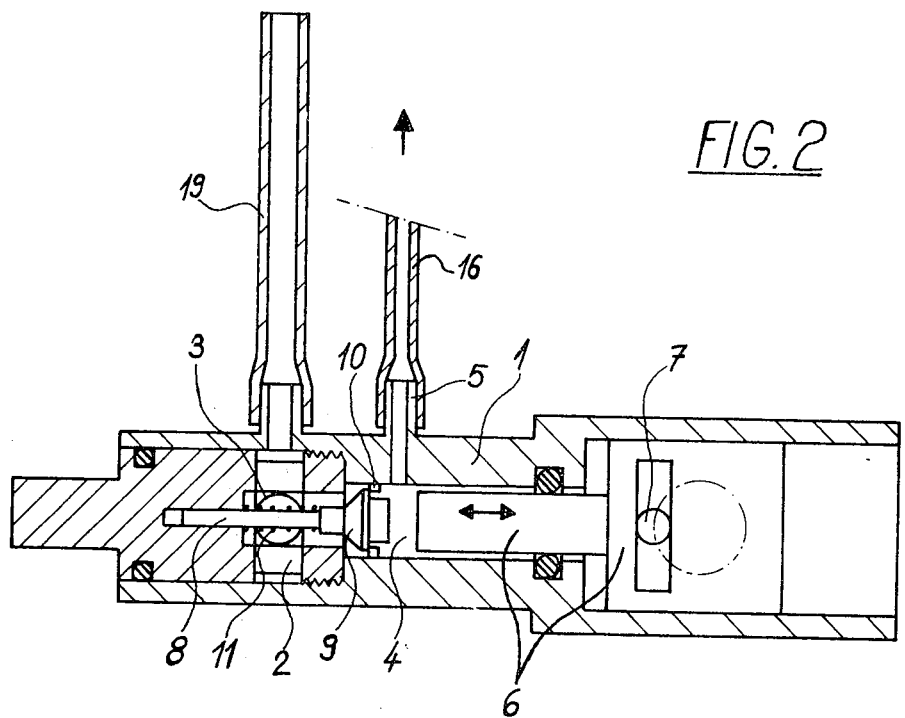
Figure 3:
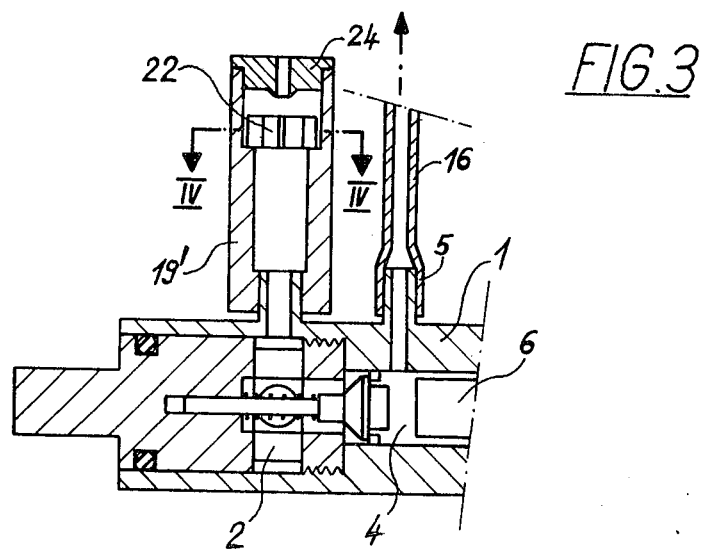
Figure 4:
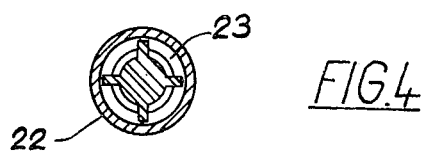

Two embodiments of the invention are described in detail with reference to the drawings:

FIG. 1 is a diagrammatic illustration of the hand-operated appliance according to the invention, partly in section, FIG. 2 is a section on line II—II of FIG. 1, FIG. 3 is an illustration according to FIG. 2 of a further embodiment, in which the ascending pipe is constructed in a different manner and FIG. 4 is a section on line IV—IV of FIG. 3.

According to FIGS. 1 and 2, the hand-operated appliance comprises a liquid pump with a pump housing 1, in which are provided an inlet chamber 2 connected to a liquid inlet pipe 3 and a working chamber 4 connected to a liquid outlet pipe 5, which working chamber is located coaxially with respect to the inlet chamber 2. Located in the working chamber is an axially reciprocating piston 6, which is driven by a drive pin 7 engaging through a slot in the rear part of the piston. This drive pin 7 is attached to the shaft of an electric motor (not shown), eccentrically with respect to the axis of the shaft and when the motor is running, moves on the circumference of the circle shown in dot-dash line in FIG. 2.

An inlet valve arranged in axial direction of the pump chambers is located with its valve stem 8 in the inlet chamber and projects into the working chamber 4 solely by its conically constructed closure member 9. In the inoperative position illustrated in FIG. 2, the inlet valve is kept in its open position by a valve spring 11 constructed as a compression spring, in the form of a helical spring surrounding the valve stem 8, which open position is determined by stops 10 on the inner wall of the working chamber 4. In this position, the connection between the inlet chamber and working chamber is fully open. The dimensions of the valve displacement determined by the stops 10 are so small that the displacement time of the inlet valve during operation is as short as possible.

According to FIG. 1, located adjacent the pump housing 1 is a hollow support 14, on which may be placed a liquid reservoir 12 open at the top. The reservoir 12 has a lower opening 13 which is closed by known means (not shown), when the reservoir is removed from the support 14 and which is automatically freed when placing the reservoir on the support and connected to the inner channel of the hollow support 14. The outlet aperture of the hollow support 14 is connected to the inlet pipe 3 of the pump by a connecting pipe 15.

The outlet pipe 5 of the pump is connected by a flexible hose 16 to the housing of a spray nozzle 17 constructed as a handle, which comprises a stop valve 18 operated by the user, on the periphery of the nozzle handle. In the closed position of the stop valve 18, the supply of liquid to the nozzle aperture is stopped, whereas in the open position of the stop valve 18, the liquid supplied by the pump may leave through the nozzle aperture.

Branching from the inlet chamber 2 of the pump is a vertical ascending pipe 19, placed on a corresponding connecting piece 20, which ascending pipe 19 is open at the top and together with the inlet chamber 2 of the pump, the connecting pipe to the reservoir 12 and this reservoir, forms a system of communicating pipes. Ribs 21 provided in the pump inlet chamber 2 form baffles by which it is achieved that the liquid reaching the ascending pipe 19 through the inlet chamber 2, after placing the full reservoir 12 on the support 14 circulates satisfactorily around the inlet valve 8, 9 and also that at least a small portion of the liquid passes through the open inlet valve into the operating chamber 4. The arrangement and dimensions of the ascending pipe 19 and of the inlet chamber 2 are such that the liquid levels in the reservoir 12 and in the ascending pipe 19 may equalize in an unhindered manner during operating as far as possible without the formation of air pockets.

When the hand-operated appliance according to the invention, which is empty or only partly filled with liquid, is to be used once more after an interval and the full reservoir 12 is placed on the support 14 for this purpose, then even when the stop valve 18 is closed, the inlet chamber 2 of the pump may immediately fill completely with liquid, because the liquid flowing into the inlet chamber expels all the air through the ascending pipe 19 and rises in the latter until the liquid head in the ascending pipe 19 has reached the same level as in the reservoir 12. Simultaneously, liquid cleans and circulates around the inlet valve 8, 9, a prerequisite which is important for the immediate initiation of conveyance by the pump on opening the stop valve. Furthermore, at least a few drops of liquid pass into the pump working chamber 4. Now, when the pump motor is switched on, the pump starts up immediately, since the inlet valve 8, 9 is open and during the first part of the working stroke of the piston 6, allows the escape of expelled liquid into the inlet chamber 2, which is connected to the ascending pipe 19 and the reservoir 12. If the pressure in the working chamber increases during the second part of the working stroke, the inlet valve closes against the action of the valve spring 11, whose strength is chosen to be sufficiently low and needs solely to be so weak that the inlet valve is reliably open in its inoperative position. At the end of the working stroke of the piston, when the pressure has reduced sufficiently, the inlet valve opens once more, the following suction stroke of the piston promoting and accelerating this opening movement, in particular at the full speed of the pump.

Thus, since the closing of the inlet valve takes place in a somewhat delayed manner with respect to the beginning of a working stroke of the piston, the pump may start up virtually without load and reach its operating speed quickly, even when the working chamber 4 and outlet pipe 16 are filled with liquid as far as the closed stop valve 18.

Now, when the stop valve is opened, the supply of liquid to the spray nozzle 17 begins immediately, since on account of the ascending pipe 19, at least in the region of the inlet chamber of the pump, the hydraulic system is satisfactorily vented and completely filled with liquid and it is not necessary, first of all, to remove pockets of air from the pump inlet chamber. As shown in tests, for normal operation of the hand-operated appliance, the closing delay of the inlet valve has no function; the hand-operated appliance thus operates just as well as hand-operated appliances with an inlet valve actuated by a closing spring.

As regards the inlet valve, the apparatus according to the invention thus requires no additional expenditure, compared with hand-operated appliances known hitherto and the problem of immediate starting-up of the pump when the motor is switched on is solved without any additional constructional means. Also, the provision of a simple ascending pipe does not cause any constructional difficulties and represents a measure which hardly makes the appliance more expensive, but which solves the problem of venting in an optimum manner.

In the example according to FIGS. 3 and 4, the height of the ascending pipe 19' is less than that of the reservoir 12, which is advantageous for reasons of space. The open upper side of the ascending pipe 19' is covered by a cover 24 provided with a central opening and a float 22 is provided in the ascending pipe, which float has openings 23 for the passage of air according to FIG. 4. The arrangement is such that when the ascending pipe 19' is completely full, in its upper position, the float 22 seals the central opening in the cover 24 with its central seat.

The ascending pipe has the additional advantage that when the appliance is not in use, the inside of the pump is connected to the atmosphere by way of the ascending pipe, so that liquid contained in the pump may evaporate, which is desirable for reasons of hygiene. Stagnating liquid is thus prevented from remaining in the pump over a prolonged period. A further advantage of the ascending pipe, which has only a relatively small diameter, consists in that the latter is located in the immediate vicinity of the connecting opening between the inlet chamber and working chamber, which facilitates the expulsion of liquid from the working chamber into the full inlet chamber during the starting-up of the pump, when the stop valve is closed, since the liquid in the inlet chamber may escape directly into the ascending pipe. The liquid head in the ascending pipe, which is only relatively slender, thus has slight inertia compared with the mass of liquid located in the reservoir 12, in the pipe 15 and 3 as well as in the pump inlet chamber 2 and may therefore yield virtually without delay under the action of the pressure or suctional forces produced by the piston 6, at the same time, the friction to be overcome of the moving mass of liquid on the walls of the ascending pipes being only slight. For the same reason, the conveyance of liquid during normal operation is facilitated and improved, since the ascending pipe acts a small, virtually inertia-free liquid reservoir in the immediate vicinity of the inlet valve, which supplies the pump immediately and without delay, whereas the liquid flows only slowly out of the reservoir 12.

The pump may also be constructed such that the working chamber is located vertically below the inlet chamber and the inlet valve is arranged vertically with its closing part pointing downwards. Then, the inlet valve assumes its open position under the action of gravity and an opening spring may be dispensed with.

What is claimed is:

1. Hand-operated appliance for body care by means of an intermittent liquid jet, in particular for massaging the gums and for cleaning the teeth, comprising: a liquid pump which comprises a working chamber, an outlet pipe connected to said working chamber, a piston reciprocable axially therein and driven by an electric motor, an inlet chamber, an inlet pipe connected to said inlet chamber, and an inlet valve located in the connecting aperture between the inlet chamber and working chamber, which valve is closed at the time of the working stroke of the piston and opened at the time of the suction stroke; a liquid reservoir connected to the inlet pipe; a spray nozzle connected to the outlet pipe; and a stop valve actuated by the user for opening and closing the pipe leading to the spray nozzle aperture, and wherein the inlet valve is constructed and arranged such that is assumes its open position in the inoperative position, when the pump is switched off.

2. Hand-operated appliance according to claim 1, further comprising a spring biasing the inlet valve towards the open position, wherein the spring force is less than the pressure exerted during the working stroke of the piston and tending to close the valve.

3. Hand-operated appliance according to claim 2, in which the inlet valve has a valve stem located in the inlet chamber and a closure member projecting into the working chamber, in which said closure member is a helical spring surrounding the valve stem.

4. Hand-operated appliance according to claim 1, wherein in the normal operating position of the pump, the inlet valve is arranged at least approximately vertically and with its closure member directed downwards so that in its inoperative position, it assumes its open position under the action of gravity.

5. Hand-operated appliance according to claim 1, further comprising stops for limiting the travel of the inlet valve to determine the open inoperative position of the inlet valve.

6. Hand-operated appliance according to claim 1, in which the liquid reservoir is connected by the inlet chamber of the pump to an ascending pipe acting as an air-vent pipe, arranged vertically and open at the top, which branches from the inlet chamber.

7. Hand-operated appliance according to claim 6, in which the height of the ascending pipe is less than that of the reservoir, and a float provided with apertures for the passage of air is arranged in this ascending pipe, said float, in its raised position, sealing off the upper aperture of the ascending pipe with its seat, when the ascending pipe is completely full.

8. Hand-operated appliance according to claim 6, further comprising baffles arranged inside the inlet chamber so that the liquid penetrating the inlet chamber and the ascending pipe from the full reservoir circulates completely around the inlet valve and passes at least partly through the open inlet valve into the working chamber of the pump.

9. Hand-operated appliance for body care by means of an intermittent liquid jet, in particular for massaging the gums and for cleaning the teeth, comprising a liquid pump which comprises a working chamber, an outlet pipe connected to the working chamber, a reciprocable piston disposed within the working chamber and driven by a motor, an inlet chamber, an inlet pipe connected to the inlet chamber, and an inlet valve located in the connecting opening between the inlet chamber and working chamber; a liquid reservoir connected to the inlet pipe; a spray nozzle connected to the outlet pipe; and a vertical ascending pipe extending upward from the inlet chamber and in communication therewith and having an open upper end to define an air-vent, wherein the liquid reservoir is connected by the inlet chamber of the pump to the ascending pipe acting as an airvent pipe.

10. Hand-operated appliance according to claim 9, in which the height of the ascending pipe is less than that of the reservoir, and a float provided with openings for the passage of air and disposed within the ascending pipe, which float seals the upper opening of the ascending pipe with a seat in its raised position, when the ascending pipe is completely full of liquid.

11. Hand-operated appliance according to claim 9, further comprising baffles arranged inside the inlet chamber so that the liquid entering the inlet chamber and ascending pipe from the full reservoir connected to the pump circulates completely around the inlet valve.

12. Hand-operated appliance according to claim 11, further comprising a stop valve operated by the user for opening and closing the pipe leading to the spray nozzle aperture, and in which the inlet valve is constructed and located such that it assumes its open position in the inoperative position when the pump is switched off.

13. Hand-operated appliance according to claim 12, further comprising a spring biasing the inlet valve towards the open position, wherein the spring force is less than the pressure exerted during the working stroke of the piston and tending to close the valve.

14. Hand-operated appliance according to claim 13, in which the inlet valve has a valve rod located in the inlet chamber and a closure member projecting into the working chamber, said closure member being a helical spring surrounding the valve stem.

15. Hand-operated appliance according to claim 12, wherein in the normal operating position of the pump, the inlet valve is arranged at least approximately vertically and is directed with its closure member downwards so that in its inoperative position it assumes its open position under the action of gravity.

16. Hand-operated appliance according to claim 12, further comprising stops for limiting the travel of the inlet valve to determine the open inoperative position of the inlet valve.

17. Hand-operated appliance according to claim 12, in which the inside of the pump is constructed such that after connecting the full reservoir to the pump, the liquid entering the latter passes at least partially through the open inlet valve into the working chamber.

* * * * *